(12) United States Patent
Attinger et al.

(10) Patent No.: US 6,685,725 B2
(45) Date of Patent: Feb. 3, 2004

(54) SURGICAL INSTRUMENT

(75) Inventors: Jürg Attinger, Stein am Rhein (CH); Heinrich Hedinger, Wilchingen (CH)

(73) Assignee: Alcon Grieshaber AG, Schaffhausen (CH)

( * ) Notice: Subject to any disclaimer, the term of this patent is extended or adjusted under 35 U.S.C. 154(b) by 0 days.

(21) Appl. No.: 10/094,783

(22) Filed: Mar. 11, 2002

(65) Prior Publication Data

US 2002/0143363 A1 Oct. 3, 2002

(30) Foreign Application Priority Data

Mar. 29, 2001 (EP) .......................................... 01810318

(51) Int. Cl.[7] .............................................. A61B 17/50
(52) U.S. Cl. ...................................... 606/210; 606/208
(58) Field of Search .............................. 606/205–210, 606/119–122, 142, 145, 148, 160, 161

(56) References Cited

U.S. PATENT DOCUMENTS

| | | | |
|---|---|---|---|
| 2,214,984 A | 9/1940 | Bachmann | |
| 3,815,609 A * | 6/1974 | Chester | 606/210 |
| 4,461,297 A | 7/1984 | Sutter | |
| 4,724,838 A * | 2/1988 | Hasson | 606/148 |
| 4,761,028 A * | 8/1988 | Dulebohn | 606/210 |
| 4,844,065 A | 7/1989 | Faulkner | |
| 5,312,420 A * | 5/1994 | Toso et al. | 606/206 |

FOREIGN PATENT DOCUMENTS

GB 769 917 A 3/1957

* cited by examiner

*Primary Examiner*—Kevin T. Truong
(74) *Attorney, Agent, or Firm*—Henry M. Feiereisen; Ursula B. Day

(57) ABSTRACT

A surgical instrument, in particular ophthalmologic clamp, includes two substantially parallel spring arms interconnected at their rear end and having a forward end terminating in clamping elements. An actuating mechanism is provided for moving the spring arms relative to one another in opposition to a spring elastic restoring force of the spring arms to thereby implement an inverse movement of the clamping elements. The actuating mechanism includes two plate-shaped operating members and four pins, whereby the pins are so disposed that two pins are connected to one operating member and the distal one of the spring arms, and two pins are connected to the other operating member and the other of the spring arms.

20 Claims, 2 Drawing Sheets

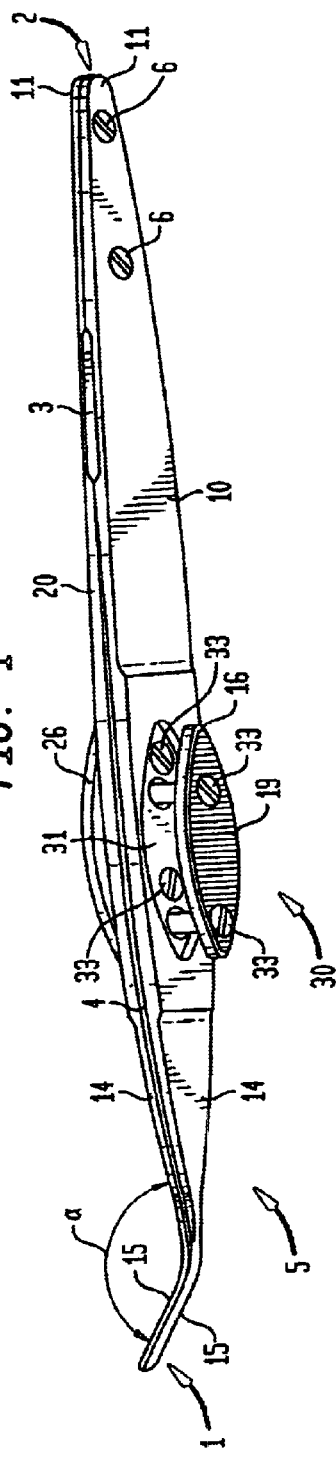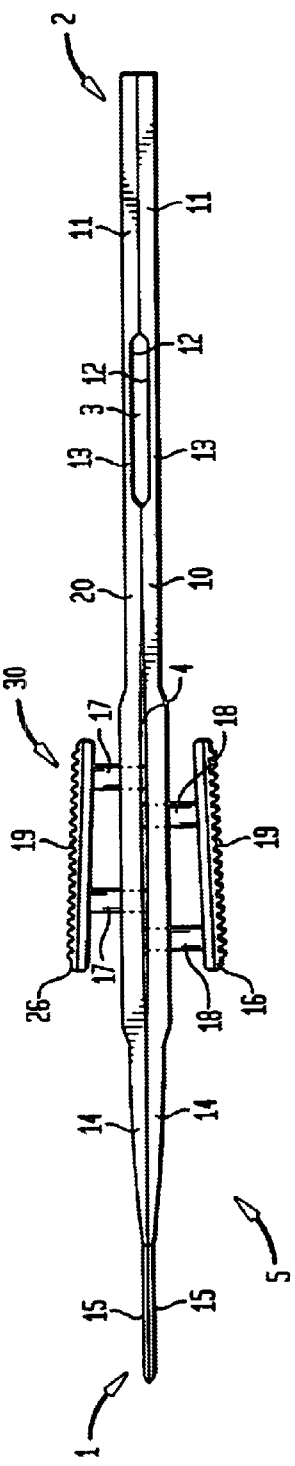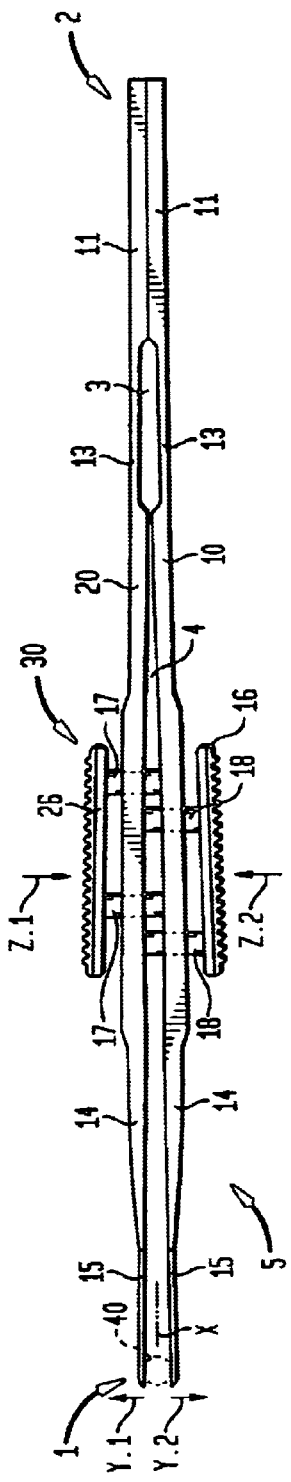

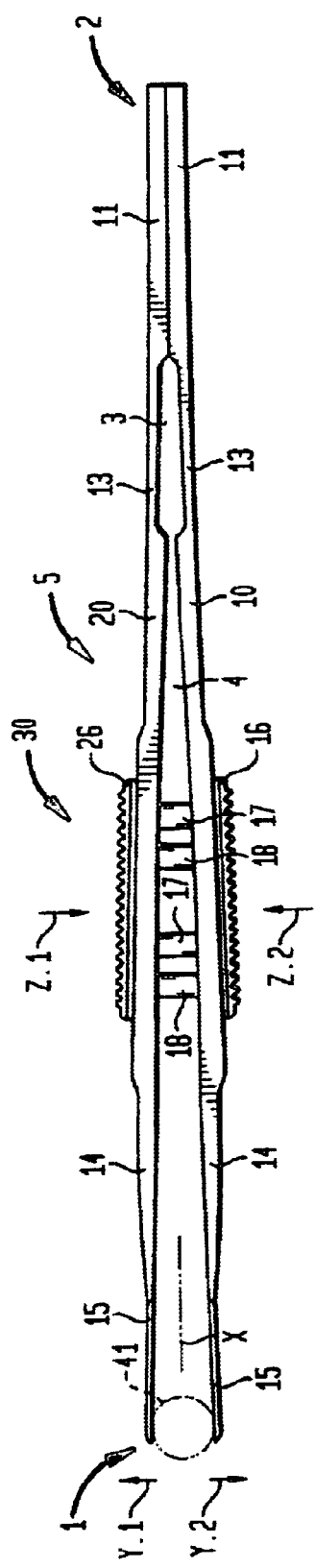
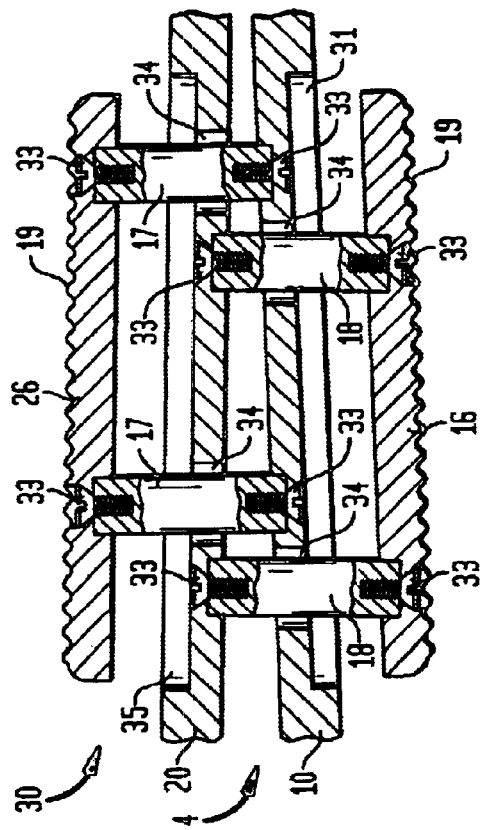

SURGICAL INSTRUMENT

CROSS-REFERENCES TO RELATED APPLICATIONS

This application claims the priority of European Patent Application Serial No. 01 810 319.2, filed Mar. 29, 2001, the subject matter of which is incorporated herein by reference.

BACKGROUND OF THE INVENTION

The present invention relates, in general, to a surgical instrument, and more particularly to a surgical clamping instrument.

British Pat. No. 769,917 discloses a clamping instrument in the form of tweezers which includes two spaced-apart spring arms in parallel relationship. At their one end, the spring arms are connected to a spacer block, placed in-between the spring arms. A setting screw is provided to adjust the spring-elastic restoring force of the spring arms. At the other end, the spring arms are inwardly bent for detachable securement of jaws. Each spring arm further includes an arched pin which extends through a hole in the other spring arm and has a disk-like actuating member for moving the jaws apart to thereby allow grasping and holding of an object.

U.S. Pat. No. 4,844,065 discloses a clamping instrument in the form of a forceps for inserting a deformable intraocular lens. The clamping instrument has two elongate spring arms in crossing configuration, which are spaced from one another at their front end by a spacer and have angled ends to form jaws for grasping and holding the lens.

Other clamping instruments in the form of tweezers or forceps are known, for example, from U.S. Pat. Nos. 2,214,984 and 4,461,297. Their configuration is, however, very complicated and they are unsuitable for insertion and implanting a deformable lens into the eye of a living being.

Microsurgical procedures, in particular ophthalmologic surgical procedures increasingly demand instruments that are precise when it comes to grabbing an object while yet being easy to handle. Conventional instruments of this kind have shortcomings because the ophthalmologist is restricted in his or her mobility when, e.g., guiding an artificial lens to be implanted through an incision or to maintain an incised tissue flap manually in folded position to clear the surgical area.

It would therefore be desirable and advantageous to provide an improved surgical instrument, which obviates prior art shortcomings and ensures a precise handling during surgical procedures such as implanting an artificial lens or grasping an incised tissue part.

SUMMARY OF THE INVENTION

According to one aspect of the present invention, a surgical instrument, in particular ophthalmologic clamp, includes two spring arms disposed in substantial parallel relationship and interconnected on one end, two clamping elements, respectively connected to the other end of the spring arms, and an actuating mechanism for moving the spring arms relative to one another in opposition to a spring elastic restoring force of the spring arms to thereby implement an inverse movement of the clamping elements, wherein the actuating mechanism includes two plate-shaped operating members in parallel disposition to the spring arms, and four pins, with two pins disposed in spaced-apart relationship in longitudinal direction and having one end connected to one of the operating members and another end operatively connected to a confronting one of the spring arms, and two pins disposed in spaced-apart relationship in longitudinal direction and having one end connected to the other one of the operating members and another end operatively connected to other one of the spring arms.

The present invention resolves prior art problems by so arranging the spaced-apart pins that each of the pins extends between an operating member and a distal one of the spring arms so as to ensure a precise opening and closing of the clamping elements relative to one another.

According to another feature of the present invention, the actuating mechanism may be so configured that a movement path of the clamping elements into an opening direction is determined by a distance that the operating members can move into abutment with the spring arms. Suitably, the spring arms may each have an indentation for receiving the operating members, when the operating members are press together.

According to another feature of the present invention, the operating members may have a roughened outer surface and received in the indentations of the spring arms except for the roughened outer surface.

BRIEF DESCRIPTION OF THE DRAWING

Other features and advantages of the present invention will be more readily apparent upon reading the following description of currently preferred exemplified embodiments of the invention with reference to the accompanying drawing, in which:

FIG. 1 is a perspective illustration, on an enlarged scale, of a surgical instrument according to the present invention in the idle, closed position;

FIG. 2 is a top plan view of the surgical instrument of FIG. 1;

FIG. 3 is a top plan view of the surgical instrument in partially opened position;

FIG. 4 is a top plan view of the surgical instrument in fully opened position; and FIG. 5 is a cutaway sectional view of the surgical instrument, showing in detail the area of actuation.

DETAILED DESCRIPTION OF PREFERRED EMBODIMENTS

Throughout all the Figures, same or corresponding elements are generally indicated by same reference numerals.

Turning now to the drawing, and in particular to FIG. 1, there is shown a perspective illustration, on an enlarged scale, of a surgical instrument according to the present invention, generally designated by reference numeral 5, for performing ophthalmologic procedures in particular. The surgical instrument 5 is configured in the form of a tweezers and includes two elongate spring arms 10, 20, which extend adjacent to and coextensive to one another, with a longitudinal slot 4 being formed therebetween. The spring arms 10, 20 have each a forward portion 14 terminating in a clamping element 15 to define together an operative tip 1. An actuating mechanism, generally designated by reference numeral 30 is operatively connected to the spring arms 10, 20 and so constructed as to effect an inverse movement of the clamping elements 15, i.e. in a direction away from one another, into an opening direction, as shown by way of example in FIGS. 3 and 4. The spring arms 10, 20 are so constructed and disposed relative to one another that the forward portions 14 together with the clamping elements 15 are pressed together as a consequence of the configuration of the spring arms 10, 20 and the application of a resultant spring-elastic restoring force.

As shown in particular in FIG. 1, the clamping elements 15 are bent upwardly with respect to the spring arms 10, 20 at an obtuse angle α in the range of 110° to 175°. A currently preferred angle a of the upward bent of the clamping elements 15 is 130°. Although not shown in the drawing, persons skilled in the art will understand that depending on the needs at hand, the clamping elements 15 of the spring arms 10, 20 may certainly also have a downwardly bent configuration, or may represent a straight prolongation of the spring arms 10, 20, without departing from the spirit of the present invention.

Both spring arms 10, 20 are interconnected at their rear end 2 (spring arm base) via respective end pieces 11 which are arranged adjacent to one another in flat engagement along their confronting inside surfaces and extend up to a recess 3. The recess 3 is defined by confronting indentations 12 in wall portions 13 of the spring arms 10, 20 at the transition to the end pieces 11, as best seen in FIG. 2. The end pieces 11 are secured together by spaced-apart screw fasteners 6. Of course, fastening means other than screw fasteners 6, are conceivable as well, such as, e.g., rivets or welded connection in order to effect an interconnection of the spring arms 10, 20.

Although the drawings show the spring arms 10, 20 of substantially rectangular cross section, persons skilled in the art will appreciate that the rectangular profile of the spring arms 10, 20 is chosen by way of example only, as other configurations are certainly conceivable as well, such as, for example, in the form of round bars.

FIG. 1 shows the surgical instrument 5 in an idle position so that the clamping elements 15 are closed as a consequence of the innate spring force of the spring arms 10, 20. By operating the actuating mechanism 30, the forward portions 14, and thus the clamping elements 15, are moved away from one another into the opening direction so as to allow a grasping and secure handling of an object by the surgeon, as shown in FIGS. 3 and 4, with FIG. 3 depicting an intermediate opening position for grabbing a smaller object 40, and FIG. 4 depicting the fully opened position for grabbing a greater object 41.

The actuating mechanism 30, which is suitably positioned approximately in mid-section between the recess 3 and the clamping elements 15, will now be described in more detail with reference to FIG. 5.

As shown in FIG. 5, the actuating mechanism 30 includes two plate-shaped operating members 16, 26, whereby the operating member 26 extends parallel to the proximate spring arm 20 and is connected to the distal spring arm 10 via two-spaced-apart pins 17. The pins 17 traverse respective bores 34 in the spring arm 20 and are secured to the operating member 26 and the spring arm 10 by screw fasteners 33 which are received with their head in counterbores in the operating member 26. In analogous manner, the operating member 16 extends parallel to the proximate spring arm 10 and is connected to the distal spring arm 20 via two-spaced-apart pins 18 which traverse respective bores 34 in the spring arm 10 and are secured to the operating member 16 and the spring arm 20 by screw fasteners 33 which are received with their head in counterbores in the operating member 16. Of course, fastening means other than screw fasteners 33 are conceivable as well, such as, e.g., rivets or welded connection in order to effect the connection between the spring arms 10, 20 and the operating members 16, 26.

The plate-shaped operating members 16, 26 are suitably provided at their spring-arm distal side with a roughened outer surface 19 through ribbing or fluting extending suitably transversely to the longitudinal direction of the spring arms 10, 20 or the operating members 16, 26.

The spring arm 10 is formed with an indentation 31 in confronting disposition to the operating member 16 whereas the spring arm 20 is formed with an indentation 35 in confronting disposition to the operating member 26. Suitably, the indentations 31, 35 are configured to complement the outer contour of the operating members 16, 26, respectively, and have a depth sufficient to at least partially accommodate the operating members 16, 26, when the operating members 16, 26 are pressed together to move the spring arms 10, 20 apart and to open the clamping elements 15. The fully open position is shown in FIG. 4.

Although not shown in the drawing, the operating members 16, 26 may also have a circular configuration.

The surgical instrument 5 can be operated as follows: In idle position, the spring arms 10, 20 are closed as shown in FIG. 2. When grabbing an object, such as object 40 in FIG. 3, the spring arms 10, 20 are moved apart by pressing the operating members 16, 26 in opposite directions as indicated by arrows Z.1, Z.2, whereby the particular connection of the operating members 16, 26 with the spring arms 10, 20 via the pins 17, 18 results in an outward deflection of the spring arms 10, 20 so that the clamping elements 15 are moved apart in directions of arrows Y.1, Y.2 with respect to a theoretical symmetry axis X for grabbing and holding the object 40.

In FIG. 4, the operating members 16, 26 are pressed together in the direction of arrows Z.1, Z2, until substantially received in the recesses 31, 35 and resting against the confronting inside wall surfaces of the spring arms 10, 20. The clamping elements 15 assume their fully open position to grab and hold the object 41.

The object 40 or 41 may represent, e.g., a tissue flap, or an artificial lens for implantation, and is held folded by the clamping elements 15 along a theoretic symmetry axis. Release of the object 40 or 41 can easily be effected by releasing the pressure on the actuating mechanism 30 so that the spring arms 10, 20 are moved together by the spring-elastic restoring force until assuming the closed idle position shown in FIG. 2. The automatic inward movement into the closing position of both clamping elements 15 is substantially realized by the spring-elastic restoring force in the area of the wall portions 13 of the spring arms 10, 20, which wall portions 13 are configured as leaf spring. As a result of the indentations 12, the wall portions 13 have a reduced thickness and are so configured and sized that a slight holding force is applied onto the grasped object 40 or 41. An inadvertent and destructive deformation and/or squashing of the object as a result of the spring-elastic restoring force of the spring arms 10, 20 is thus prevented. The surgical instrument 5 allows random movements, in particular rotational movements about the theoretical longitudinal axis.

While the invention has been illustrated and described as embodied in a surgical instrument, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A surgical instrument, in particular ophthalmologic clamp, comprising:

two spring arms defining a longitudinal axis and disposed in substantial parallel relationship, each said spring arm having first and second ends, with the first ends of the spring arms being interconnected;

two clamping elements, one clamping element connected to the second end of one of the spring arms and the other clamping element connected to the second end of the other one of the spring arms; and an actuating mechanism for moving the spring arms relative to one another in opposition to a spring elastic restoring force of the spring arms to thereby implement an inverse movement of the clamping elements, said actuating mechanism including two plate-shaped operating members, which extend in parallel relationship to the spring arms, and four pins, with two pins disposed in spaced-apart relationship in a direction of the longitudinal axis and having one end connected to one of the operating members and another end operatively connected to a confronting one of the spring arms, and two pins disposed in spaced-apart relationship in a direction of the longitudinal axis and having one end connected to the other one of the operating members and another end operatively connected to other one of the spring arms.

2. The surgical instrument of claim 1, wherein the operating members have an elongate configuration.

3. The surgical instrument of claim 1, wherein the operating members are disposed in substantial parallel relationship to the spring arms, when the clamping elements are pressed together as a consequence of the applied restoring force of spring arms.

4. The surgical instrument of claim 1, wherein the actuating mechanism is so configured that a movement path of the clamping elements into an opening direction is determined by a distance that the operating members can move into abutment with the spring arms.

5. The surgical instrument of claim 4, wherein the spring arms have each an indentation for receiving the operating members, when the operating members are press together for moving the clamping elements into the opening direction.

6. The surgical instrument of claim 5, wherein each of the operating members has a roughened outer surface and is received in the indentation of the spring arm except for the roughened outer surface.

7. The surgical instrument of claim 1, and further comprising a fastening means for detachably connecting the pins to the ends to the operating members and the spring arms.

8. The surgical instrument of claim 7, wherein the fastening means includes a screwed connection.

9. The surgical instrument of claim 7, wherein the fastening means includes a riveted connection.

10. The surgical instrument of claim 1, wherein each of the spring arms has two bores for passage of the pins in such a manner that the two pins operatively connected to the one of the spring arms traverse the bores of the other one of the spring arms, and the two pins operatively connected to the other one of the spring arms traverse the bores of the one of the spring arms.

11. The surgical instrument of claim 1, wherein the clamping elements are tapered toward their spring arm distal end.

12. The surgical instrument of claim 11, wherein the angle ranges from 110° to 175°.

13. The surgical instrument of claim 11, wherein the angle is 130°.

14. The surgical instrument of claim 1, wherein the clamping elements are bent at an obtuse angle relative to the spring arms.

15. A surgical instrument, comprising:

two elongated spring arms arranged adjacent to and coextensive to one another, each said spring arm terminating at a forward end in a clamping element, wherein the clamping element is tapered and bent at an obtuse angle; and two operating members arranged at a distance to a rear end of the spring arms on the spring arms in one-to-one correspondence, wherein the spring arms are formed with indentations complementing the operating members and adapted to receive the operating members, wherein each of the operating members is connected to the distal one of the spring arms by two spaced-apart pins for implementing an inverse movement of the clamping elements of the spring arms, wherein the inverse movement of the clamping elements is limited by the abutment of the operating members against a confronting wall portion of the spring arms.

16. A surgical instrument, comprising:

two spring arms interconnected at one end and constructed with an innate spring force to seek a closed position of the spring arms; and an actuating mechanism for deflecting the spring arms outwards in opposition to the spring force, said actuating mechanism including two operating members disposed on opposite sides of the spring arms at a distance to a proximate one of the spring arms and connected to a distal one of spring arms so that application of a force upon the operating members moves the operating members toward one another while effecting the outward deflection of the spring arms.

17. The surgical instrument of claim 16, wherein the actuating mechanism includes a pin connection for coupling the operating members to the distal ones of the spring arms.

18. The surgical instrument of claim 16, wherein the operating members have an elongate or round configuration.

19. The surgical instrument of claim 16, wherein the spring arms have indentations for receiving the operating members and thereby limit a movement path of the operating members.

20. The surgical instrument of claim 16, wherein the operating members have a roughened outer surface.

* * * * *